(12) United States Patent
Casner et al.

(10) Patent No.: US 7,153,966 B2
(45) Date of Patent: Dec. 26, 2006

(54) PREPARATION OF OXYCODONE

(75) Inventors: Michael Lawrence Casner, Pitman, NJ (US); Jen-Sen Dung, Boothwyn, PA (US); Erno M. Keskeny, Wilmington, DE (US); Jin Luo, Fulletron, CA (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 11/234,627

(22) Filed: Sep. 23, 2005

(65) Prior Publication Data

US 2006/0111383 A1 May 25, 2006

(30) Foreign Application Priority Data

Sep. 23, 2004 (GB) .................................. 0421149.6

(51) Int. Cl.
*C07D 489/08* (2006.01)
*C07D 489/04* (2006.01)
(52) U.S. Cl. .......................................... 546/45; 546/44
(58) Field of Classification Search ................. 546/45, 546/44
See application file for complete search history.

(56) References Cited

U.S. PATENT DOCUMENTS

| 6,008,355 A | 12/1999 | Huang et al. |
| 6,090,943 A | 7/2000 | Mudryk et al. |
| 6,177,567 B1 | 1/2001 | Chiu et al. |
| 6,262,266 B1 | 7/2001 | Chiu et al. |
| 6,403,798 B1 | 6/2002 | Chiu et al. |
| 6,864,370 B1 | 3/2005 | Lin et al. |
| 2005/0222188 A1 | 10/2005 | Chapman et al. |

FOREIGN PATENT DOCUMENTS

EP  0 889 045 A1  1/1999

OTHER PUBLICATIONS

Roland Kraβnig et al., "Optimization of the Synthesis of Oxycodone and 5-Methyloxycodone," *Arch. Pharm. Pharm. Med. Chem.*, vol. 329, 1996, pp. 325-326.

*Primary Examiner*—Charanjit S. Aulakh
(74) *Attorney, Agent, or Firm*—RatnerPrestia

(57) ABSTRACT

A process for preparing oxycodone or an oxycodone salt, wherein the oxycodone or oxycodone salt has low levels of impurities (especially 14-hydroxycodeinone) is disclosed. The process comprises the steps of:
  a) preparing a mixture comprising oxycodone and a solvent and adjusting the pH of the mixture to less than 6; and subsequently
  b) exposing the mixture to hydrogenation reagents for a period of at least 1 hour.

12 Claims, No Drawings

PREPARATION OF OXYCODONE

CROSS REFERENCE TO RELATED APPLICATIONS (IF APPLICABLE)

This application claims priority of British Patent Application No. 0421149.6, filed Sep. 23, 2004

FIELD OF THE INVENTION

The present invention relates to a process for preparing oxycodone having low levels of impurities. In particular, the process is useful for preparing oxycodone with low levels of α,β-unsaturated ketones.

BACKGROUND OF THE INVENTION

Oxycodone is a narcotic analgesic having the structure (I):

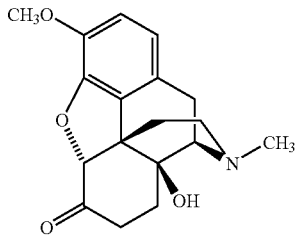

Oxycodone can be manufactured from the natural product thebaine (II) by a well-known process as disclosed in U.S. Pat. No. 6,090,943:

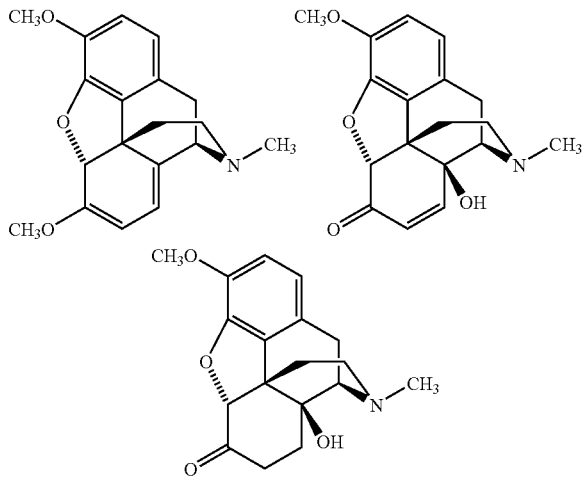

Thebaine (II) or a salt thereof is reacted with hydrogen peroxide in isopropanol, water and formic acid, producing 14-hydroxycodeinone (III). The double bond in the 14-hydroxycodeinone (III) is reduced by reaction with hydrogen in the presence of a Pd/BaSO$_4$ catalyst, providing oxycodone (I).

SUMMARY OF THE INVENTION

Recently there has been a concern about the presence of α,β-unsaturated ketone impurities in pharmaceutical products. 14-hydroxycodeinone (III) is an α,β-unsaturated ketone, and unsurprisingly, small quantities of this compound may be found in oxycodone (I). The present inventors have sought to provide a method for preparing oxycodone having low levels of impurities and in particular, low levels of α,β-unsaturated ketone impurities, preferably below 10 ppm.

Accordingly, the present invention provides a process for preparing oxycodone or an oxycodone salt, wherein the oxycodone or oxycodone salt has low levels of impurities, comprising the steps of:
 a) preparing a mixture comprising oxycodone and a solvent and adjusting the pH of the mixture to less than 6; and subsequently
 b) exposing the mixture to hydrogenation reagents for a period of at least 1 hour.

The inventors have found that this process surprisingly provides oxycodone with low levels of α,β-unsaturated ketone impurities, i.e. 14-hydroxycodeinone at less than 15 ppm. The inventors have found that in order to achieve low levels of 14-hydroxycodeinone, the pH must be adjusted before the hydrogenation step. Suitably the mixture is heated after the pH of the mixture is adjusted, so that the process comprises the steps of:
 a) preparing a mixture comprising oxycodone and a solvent, adjusting the pH of the mixture to less than 6 and heating the mixture at the temperature of at least 55° C. for a period of at least 1 hour; and subsequently
 b) exposing the mixture to hydrogenation reagents for a period of at least 1 hour.

This process provides oxycodone with very low levels of α,β-unsaturated ketone impurities, i.e. 14-hydroxycodeinone at less than 5 ppm.

DETAILED DESCRIPTION OF THE INVENTION

The mixture comprising oxycodone and a solvent can be prepared by a number of methods. In a first method, oxycodone base or a salt of oxycodone, prepared and isolated using any of the methods known to those skilled in the art, is mixed with a solvent to form the mixture. In a second method, 14-hydroxycodeinone is hydrogenated in a solvent using known hydrogenation reagents, thereby providing a mixture comprising oxycodone and a solvent. In a third method, a mixture comprising thebaine and a solvent is subjected to oxidation conditions (e.g. hydrogen peroxide in formic acid and water), followed by hydrogenation conditions, thereby providing a mixture comprising oxycodone and a solvent. Other methods of preparing a mixture comprising oxycodone and a solvent may be known to those skilled in the art.

The pH of the mixture is adjusted to less than 6, suitably less than 5, more suitably less than 3 and preferably about 1. The pH is suitably adjusted by the addition of a strong acid such as concentrated hydrochloric acid to the mixture. Preferably at least one equivalent of acid is added to the mixture.

The solvent in the mixture is suitably an organic solvent such as isopropanol, ethanol or SD3A (a 95:5 mixture of ethanol:methanol). Preferably the mixture further comprises water.

After the pH is adjusted, the mixture is suitably heated to a temperature of at least 55° C., preferably at least 60° C. and most preferably about 70–75° C. The temperature is suitably not higher than the boiling point of the solvent. The mixture is suitably heated for a period of at least 1 hour, preferably at least 3 hours and most preferably between 5–10 hours.

Suitable hydrogenation reagents are well known to the skilled person and typically include a hydrogenation catalyst and either hydrogen or a hydrogen transfer reagent, such as sodium hypophosphite. Preferred hydrogenation catalysts are precious metal catalysts such as palladium or platinum dispersed on a support material such as carbon or barium sulfate. In a preferred embodiment, a precious metal catalyst is added to the mixture and hydrogen is passed through the mixture at a pressure of 10 psi or more (162 kPa or more). The hydrogenation step is suitably carried out at a temperature of at least ambient, preferably at a temperature between room temperature and 70° C. The temperature should be sufficient to dissolve the solids in the mixture, thereby providing a solution. The mixture is exposed to the hydrogenation reagents for at least 1 hour, suitably at least 2 hours and preferably about 6 hours.

The product of step (b) is a mixture comprising oxycodone and a solvent. Hydrogenation catalysts may be removed by filtering the mixture. A purified oxycodone salt may be obtained from the mixture by reducing the temperature, and allowing the salt to crystallise out. For example, if hydrochloric acid was used in step (a), the hydrochloride salt of oxycodone will be produced. Alternatively, oxycodone base may be provided by adding a base such as sodium hydroxide to the mixture and allowing the mixture to cool.

If precious metal catalysts are used in the hydrogenation step, it is possible that unacceptable levels of the metals will remain in the final product (desirably the heavy metal content of the final product is less than 20 ppm). In one embodiment of the present invention, the oxycodone or oxycodone salt produced in step (b) is subjected to a further process wherein a mixture comprising the oxycodone or oxycodone salt and a solvent is treated with charcoal. Suitably the mixture is heated to a temperature of approx. 60–65° C., the charcoal is added, the mixture is stirred at 60–65° C. for 5 to 10 hours and the hot mixture is filtered to remove the charcoal. Cooling the hot mixture provides the oxycodone salt or oxycodone. Suitably the weight ratio of oxycodone or oxycodone salt to charcoal is between 20:1 and 1:1, preferably about 5:1. The charcoal is suitably a charcoal such as Darco® G-60 (Norit, USA).

Oxycodone or an oxycodone salt produced according to the process of the invention has low levels of α,β-unsaturated ketones and is advantageously incorporated into pharmaceutical products.

EXAMPLES

The following examples are illustrative but not limiting of the invention.

Preparation of Oxycodone Base: Route A

Thebaine (15.94 g) was added to a 250 ml flask. Water (18 ml) was added and the mixture was stirred at room temperature. Formic acid (42 ml) was added over 3 minutes and then the mixture was cooled in an ice bath. Hydrogen peroxide (30%, 6.7 g) was added and the mixture was stirred for 1 hour. The mixture was removed from the ice bath, allowed to warm to room temperature and then heated to 48° C. for 2 hours. The mixture was transferred to a hydrogenation bottle. A 5 wt % palladium on carbon catalyst (2 g) was added and hydrogen was passed through the mixture at approximately 20 psi for 15 hours. The catalyst was removed by passing the mixture through a pad of celite and rinsing the filtered solid with water/formic acid (3:1, 8 ml). The mixture was cooled in an ice bath and 25% sodium hydroxide (109 ml) was added dropwise over 50 minutes to increase the pH to 9–10. The mixture was stirred for 1 hour and 15 minutes and the solid product was filtered, rinsed with cold water and dried under vacuum pump for 3 hours. The product was oxycodone base (14.152 g, 87.7% yield) and contained 178 ppm of the α,β-unsaturated ketone impurity, 14-hydroxycodeinone.

Preparation of Oxycodone Base: Route B

Thebaine (100.0 g dry weight) was dissolved in 85% formic acid (252.3 g). 30% Hydrogen peroxide (43.6 g) was added over a period of about two hours. The mixture was stirred for three hours. Ammonium hydroxide solution was added to the mixture to increase the pH to 8–9. The solid precipitate was filtered and washed with water and ethanol. The solid was dried on the filter and in an oven. The product was 14-hydroxycodeinone (150.52 g damp, 75.32 g dry weight, 75% yield).

The 14-hydroxycodeinone (39.45 g of the damp solid) was dissolved in water (81.13 ml) and 80% acetic acid (16.17 ml). 10 wt % palladium on carbon catalyst (0.33 g wet weight, 0.16 g dry weight) was added and hydrogen was passed through the mixture for about 6 hours at about 12 psi. The mixture was filtered to remove the catalyst. An ammonium hydroxide solution was added to the mixture up to pH 9. The solid precipitate was washed with water and with ethanol, and was dried. The product was oxycodone (18.8 g, 79% yield).

Comparative Example 1

Heating and Recrystallisation of Oxycodone 13.257 g of oxycodone prepared via Route A was added to a 250 ml flask. An ethanol/methanol mixture (70 ml) was added to the flask and the mixture was stirred at room temperature, heated to reflux (78° C.) for 1 hour, cooled to room temperature and then stirred at room temperature. The mixture was cooled in an ice bath for 30 minutes and the solid product was filtered and rinsed with an ethanol/methanol mixture. The solid was dried under vacuum for 3 hours. The product was oxycodone base (11.393 g, 85.95%) and contained 210 ppm of the α,β-unsaturated ketone impurity, 14-hydroxycodeinone.

Dissolving the oxycodone, heating to 78° C. for 1 hour and recrystallising did not reduce the amount of 14-hydroxycodeinone in the oxycodone.

Comparative Example 2

Heating and Recrystallisation of Oxycodone 11 g of the oxycodone product from comparative example 1 was added to a 250 ml flask. An ethanol/methanol mixture (55 ml) was added to the flask and the mixture was stirred at room temperature, heated to reflux (78° C.) for 1 hour, cooled to room temperature and then stirred at room temperature. The mixture was cooled in an ice bath for 35 minutes and the solid product was filtered and rinsed with an ethanol/methanol mixture. The solid was dried under vacuum overnight. The product was oxycodone base (10.682 g, 97.1%) and contained 165 ppm of the α,β-unsaturated ketone impurity, 14-hydroxycodeinone.

A second step of dissolving the oxycodone, heating to 78° C. for 1 hour and recrystallising did not significantly reduce the amount of 14-hydroxycodeinone in the oxycodone.

Example 1

Preparation of Oxycodone Hydrochloride Having Low Level of Impurities 5 g of oxycodone product from comparative example 2 was added to a 100 ml flask. Water (10 ml) and isopropanol (10 ml) were added and the mixture was stirred. Concentrated hydrochloric acid (2.64 ml) was added. The mixture was heated to 75° C. for 10 hours and stirred at ambient temperature overnight. The mixture was transferred to a hydrogenation bottle and was heated to 45° C. 5 wt % palladium on carbon catalyst (0.5 g) was added to the mixture and hydrogen was passed through the mixture at about 12 psi for 6.5 hours. The mixture was warmed to 55° C., passed through a filter paper, cooled to room temperature and then placed in an ice bath for 30 minutes. The solid product was filtered, rinsed with cold isopropanol and dried overnight under a vacuum pump. The product was oxycodone hydrochloride (5.533 g, 99.2%) and contained less than 2 ppm 14-hydroxycodeinone (measured by HPLC and MS-SIM (mass spectrometry with selected ion monitoring)).

Example 2a

Preparation of Oxycodone Base Having Low Level of Impurities 1.2 g of crude oxycodone prepared via Route A was added to a 50 ml flask. Water (3.6 ml), isopropanol (3.6 ml) and formic acid (4.8 ml) were added. Concentrated hydrochloric acid (0.24 ml) was added. The mixture was heated to 75° C. and stirred at 75° C. for 10 hours. The mixture was cooled to room temperature and stirred. HPLC showed that the level of 14-hydroxycodeinone in the oxycodone increased during the heating step. Treatment with acid and heating does not prepare oxycodone with a low level of impurities.

The mixture was transferred to a hydrogenation bottle. 5 wt % palladium on carbon catalyst (120 mg) was added to the mixture and hydrogen was passed through the mixture at room temperature and about 12 psi for 24 hours. The mixture was passed through a pad of celite and then placed in an ice bath. 50% sodium hydroxide (5.3 ml) was added dropwise over 17 minutes to a pH of 9–10. The mixture was stirred at 0–5° C. for 1 hour and 10 minutes. The solid product was filtered, rinsed with cold water and dried under a vacuum pump for four hours. The product was oxycodone base (1.072 g, 89.33%) and contained approximately 3 ppm 14-hydroxycodeinone (measured by MS-SIM).

Example 2b

Preparation of Oxycodone Hydrochloride Having Low Level of Impurities 0.8 g of oxycodone base produced in Example 2a was added to a 50 ml flask. Water (1.6 ml) and isopropanol (3.76 ml) were added. Concentrated hydrochloric acid (0.32 ml) was added and the mixture was heated to 73° C. After 5 minutes at 73° C. the mixture was cooled to room temperature and was then stirred at room temperature for 1 hour. The mixture was placed in an ice bath and stirred for 1.5 hours. The solid product was filtered, rinsed with cold isopropanol and dried under a vacuum pump overnight. The product was oxycodone hydrochloride (0.892 g) and contained approximately 5 ppm 14-hydroxycodeinone (measured by MS-SIM).

Example 3

Preparation of Oxycodone Hydrochloride Having Low Level of Impurities 18.8 g oxycodone prepared via Route B was added to a flask containing ethanol (43.9 ml) and water (10.14 ml). Ethanol (5.71 ml) and concentrated hydrochloric acid (7.37 ml) were mixed and then added to the flask, providing a mixture with a pH of 1. The mixture was heated at 75° C. for 5 hours and was then cooled to 65° C. The mixture was hydrogenated at 10–12 psi for six hours using a 10 wt % palladium on carbon catalyst (175.6 mg wet weight, 88 mg dry weight). The mixture was filtered to remove the catalyst and cooled. The solid product was filtered and washed with ethanol. The product was oxycodone hydrochloride (20.13 g, 75.3%) and contained approximately 0 ppm 14-hydroxycodeinone.

Comparative Example 3a

Hydrogenation of Oxycodone 3 g of crude oxycodone prepared by essentially the same method as route A and containing 535 ppm 14-hydroxycodeinone was added to a hydrogenation bottle. Isopropanol (9 ml), water (9 ml) and formic acid (12 ml) were added. The mixture was hydrogenated for 23 hours using a 5 wt % palladium on carbon catalyst (0.3 g). The mixture was passed through a pad of celite and the hydrogenation bottle was rinsed with isopropanol and water. The mixture was cooled in an ice bath. 50% sodium hydroxide (14 ml) was added dropwise over 22 minutes to a pH of 9–10. The mixture was stirred at 0–5° C. for 1 hour and 20 minutes. The solid product was filtered, rinsed with cold water and dried under a vacuum pump overnight. The product was oxycodone base (2.822 g, 94.1%) and contained approximately 26 ppm 14-hydroxycodeinone (measured by HPLC). The hydrogenation step reduced the amount of 14-hydroxycodeinone in the oxycodone, but this method, wherein the pH of the mixture was not adjusted before the hydrogenation, did not afford oxycodone with an impurity level of less than 10 ppm.

Comparative Example 3b

Acidification of Oxycodone 2 g of oxycodone base produced in Comparative Example 3a was added to a 100 ml flask. Water (4 ml) and isopropanol (9.4 ml) were added. Concentrated hydrochloric acid (0.8 ml) was added and the mixture was heated to 70–72° C. After 5 minutes at 70–72° C. the mixture was slowly cooled to room temperature. The mixture was placed in an ice bath and stirred for 1 hour and 20 minutes. The solid product was filtered, rinsed with cold isopropanol and dried under a vacuum pump overnight. The product was oxycodone hydrochloride (2.401 g) and contained approximately 38 ppm 14-hydroxycodeinone (measured by HPLC). Adjusting the pH of the oxycodone to ~1 and heating did not further reduce the concentration of 14-hydroxycodone. Comparative Examples 3a and 3b demonstrate that oxycodone with very low level of impurities (less than 10 ppm 14-hydroxycodeinone) is not prepared by hydrogenating the oxycodone and then treating with acid.

Example 4

Preparation of Oxycodone Hydrochloride Having Low Level of Impurities 4.35 g oxycodone prepared by essentially the same method as Route B was added to a flask containing ethanol (12.5 ml) and water (2.7 ml). Concentrated hydrochloric acid (approximately 1.5 ml) was added to the flask, providing a mixture with a pH of about 2. The pH of the mixture was increased to 5 by adding ammonia. The mixture was hydrogenated at 45 psi and 50° C. for 1.5 hours and then at 10–12 psi and 50–55° C. for 4 hours using a 10 wt % palladium on carbon catalyst (0.06 g). The mixture was filtered to remove the catalyst and cooled. The solid product was filtered and washed with ethanol. The product was oxycodone hydrochloride (3.706 g, 76.1%) and contained approximately 12 ppm 14-hydroxycodeinone.

Example 5

Preparation of Oxycodone Hydrochloride Having Low Level of Impurities 3 g of oxycodone product from comparative example 2 was added to a 50 ml flask. Water (1.3 ml) and ethanol (5.58 ml) were added and the mixture was stirred. Concentrated hydrochloric acid (1.58 ml) was added. Further water was added so that in total 4.5 ml of water was added. The mixture was heated to 75° C. for 10 hours, slowly cooled to room temperature and stirred overnight. The mixture was heated to 40° C. and transferred to a hydrogenation bottle. 5 wt % palladium on carbon catalyst (0.3 g) was added to the mixture and hydrogen was passed through the mixture at between 11 and 12 psi for 6.5 hours. The mixture was warmed to 56° C. and passed through two layers of filter paper. The bottle and filtrate were rinsed with a hot solution of 1 ml water and 5 ml ethanol, and with 20 ml of hot ethanol. The filtrate was slowly cooled to room temperature and then placed in an ice bath for 30 minutes. The solid product was filtered, rinsed with cold ethanol and dried overnight under a vacuum pump. The product was oxycodone hydrochloride (2.663 g, 79.6% yield). A further 0.334 g of oxycodone hydrochloride was obtained by washing the filter cake and hydrogenation bottle with water and water/ethanol (1:1), giving a combined yield of 2.997 g and 89.5%. Both samples of oxycodone hydrochloride contained 0 ppm 14-hydroxycodeinone (measured by HPLC and MS-SIM (mass spectrometry with selected ion monitoring)).

What is claimed:

1. A process for preparing oxycodone or an oxycodone salt, comprising the steps of:
    a) preparing a mixture comprising oxycodone and a solvent, adjusting the pH of the mixture to less than 6 and heating the mixture at the temperature of at least 55° C for a period of at least 1 hour; and subsequently
    b) exposing the mixture to hydrogenation reagents for a period of at least 1 hour.

2. The process according to claim 1, wherein in step (a) the mixture is heated to a temperature of at least 60° C.

3. The process according to claim 2, wherein in step (a) the mixture is heated to a temperature of about 70–75° C.

4. The process according to claim 1, wherein in step (a) the mixture is heated for a period of between 5 to 10 hours.

5. The process according to claim 1, wherein in step (a) the pH of the mixture is adjusted to less than 5.

6. The process according to claim 5, wherein in step (a) the pH of the mixture is adjusted to less than 3.

7. The process according to claim 1, wherein the hydrogenation reagents are a hydrogenation catalyst and either hydrogen or a hydrogen transfer reagent.

8. The process according to claim 1, wherein step (b) is carried out at a temperature between ambient and 70° C.

9. The process according to claim 1, wherein in step (b) the mixture is exposed to the hydrogenation reagents for a period of at least 2 hours.

10. The process according to claim 1, wherein in step (a) the mixture is heated for a period of at least 3 hours.

11. The process according to claim 1, wherein in step (a) the mixture is heated for a period of at least 5 hours.

12. The process according to claim 1, wherein in step (a) the mixture is heated for a period between 5 and 10 hours.

* * * * *

Adverse Decision in Interference

Patent No. 7,153,966, Michael Lawrence Casner, Jen-Sen Dung, Erno M. Keskeny and Jin Luo, PREPARATION OF OXYCODONE, Interference No. 105,553, final judgment adverse to the patentees rendered March 13, 2008, as to claims 1-12 cancelled.

(*Official Gazette*, September 1, 2009)